United States Patent [19]

Schwartz

[11] Patent Number: 4,714,682
[45] Date of Patent: Dec. 22, 1987

[54] FLUORESCENT CALIBRATION MICROBEADS SIMULATING STAINED CELLS

[75] Inventor: Abraham Schwartz, Durham, N.C.

[73] Assignee: Flow Cytometry Standards Corporation, Research Triangle Park, N.C.

[21] Appl. No.: 33,625

[22] Filed: Apr. 3, 1987

Related U.S. Application Data

[60] Division of Ser. No. 805,654, Dec. 11, 1985, which is a continuation-in-part of Ser. No. 685,464, Dec. 24, 1984.

[51] Int. Cl.⁴ .................................. G01N 31/00
[52] U.S. Cl. .............................. 436/10; 427/213.32; 436/8; 436/19
[58] Field of Search ........................... 436/8–18, 436/19; 424/3; 264/4–4.7; 427/213.3–213.36

[56] References Cited

U.S. PATENT DOCUMENTS 3,412,037  11/1968  Gochman et al. .................. 436/10
4,376,059  3/1983  Davis et al. ........................ 436/10

Primary Examiner—Deborah L. Kyle
Assistant Examiner—T. J. Wallen
Attorney, Agent, or Firm—Steve J. Hultquist

[57] ABSTRACT

A method of calibrating a flow cytometer or fluorescent microscope is based on a set of highly uniform microbeads associated with a fluorescent dye in such a way that the microbeads have the same excitation and emission spectral properties as the samples which are to be measured. The calibration values of the microbeads are plotted against the relative fluorescence intensity peak channel for each microbead in the set. From this calibration plot, the relative fluorescence intensity peak channel of the sample is translated into equivalent soluble fluorescent dye molecules per sample particle. The calibration values of the standard microbeads are determined against solutions of the dyes. In cases where the background scatter of the bulk microbeads suspensions is too high for a direct determination against the solutions, a different set of microbeads with low background scatter is calibrated against the dye solutions and used to make an initial calibration of a flow cytometer or fluorescent microscope, which in turn, is used to calibrate the uniform microbead standards. A novel method of making the microbead standards is also disclosed.

3 Claims, 10 Drawing Figures

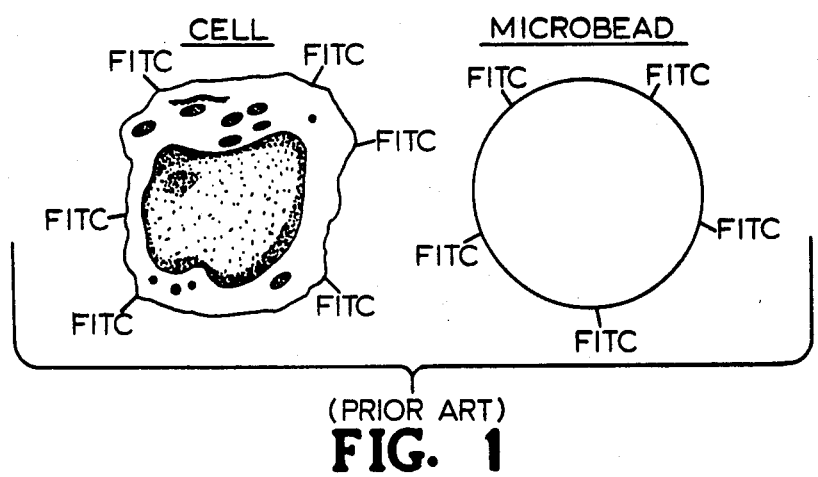
(PRIOR ART)
FIG. 1
(PRIOR ART)
FIG. 2
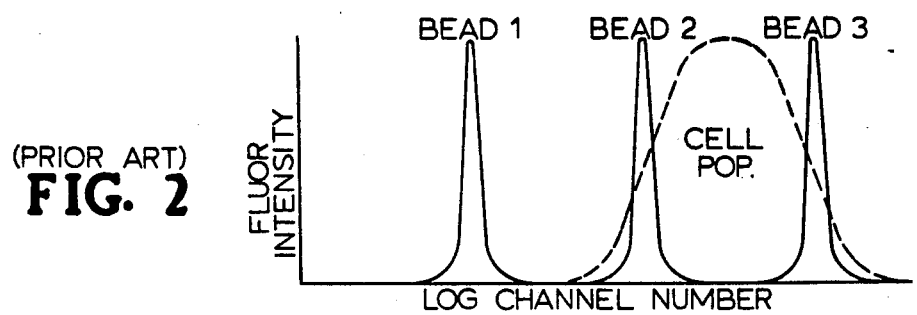
FIG. 4
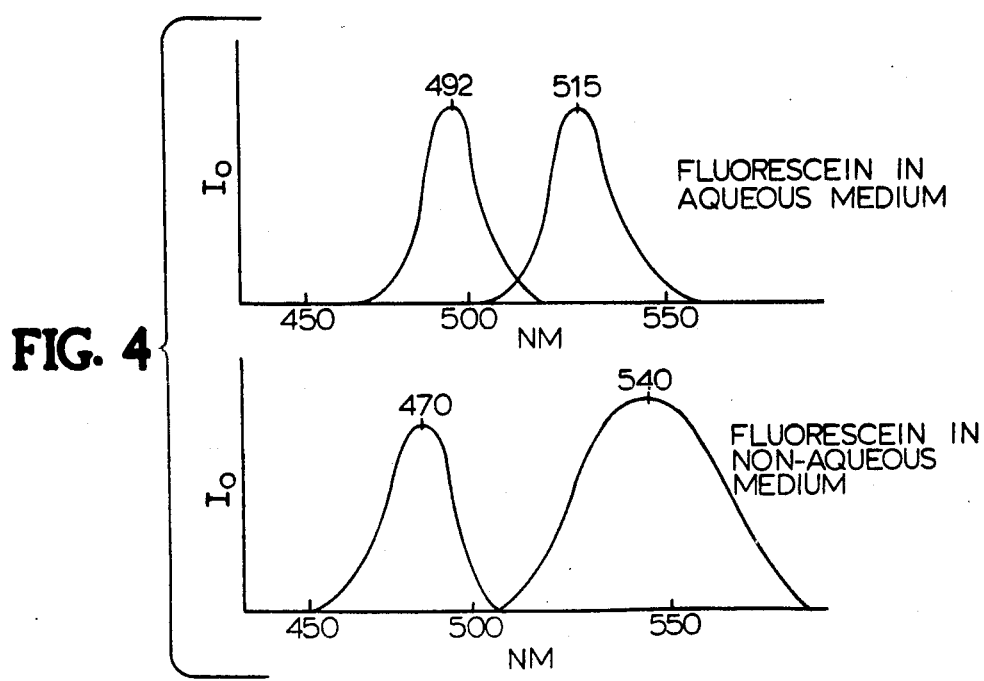

SWELL SEED BEADS WITH
OIL SOLUBLE COMPOUND
↓
SWELL BEADS WITH
MONOMER/INITIATOR
HOMOGENATE AND POLYMERIZE
↓
ANIMATE THE SURFACE
BY REACTING THE EPOXY GROUPS
WITH A DIAMINE
↓
FLUORESCENATE THE SURFACE
OF THE MICROBEADS WITH A
REACTIVE FLUORESCENT DYE

FIG. 5

MAKE REFERENCE SOLUTIONS
OF THE SOLUBLE DYE
↓
CALIBRATE THE SET OF PRIMARY
MICROBEADS AGAINST THE
FLUORESCENT REFERENCE SOLUTIONS
↓
DETERMINE THE NUMBER OF
MICROBEADS PER UNIT VOLUME AND
CALCULATE THE NUMBER OF EQUIVALENT
SOLUBLE FLUORESCENT DYE MOLECULES
PER MICROBEAD
↓
DEVELOP A CALIBRATION PLOT
ON A FLOW CYTOMETER USING
THE PRIMARY MICROBEADS
↓
CALIBRATE THE SURFACE
FLUORESCENATED MICROBEADS
ON THE CALIBRATION PLOT
DEVELOPED FROM THE
PRIMARY STANDARDS

FIG. 6

CHOOSE THE EXCITATION, EMISSION, NEUTRAL
DENSITY FILTERS, AND PMT VOLTAGE FOR THE
PARTICULAR EXPERIMENT
↓
ALIGN THE INSTRUMENT WITH THE BRIGHTEST
MICROBEAD IN THE SET THAT IS STILL WITHIN
THE RANGE OF INTEREST
↓
DETERMINE THE PEAK CHANNEL FOR EACH MICROBEAD
STANDARD, AND PLOT THEM AGAINST THE PREDETERMINED
VALUES FROM THE CALIBRATION PROCEDURE IN FIGURE 6
↓
WITHOUT CHANGING ANY OF THE ABOVE INSTRUMENT
PARAMETERS, RUN THE UNKNOWN SAMPLES AND DETERMINE THEIR
NUMBER OF EQUIVALENT SOLUBLE FLUORESCENT
MOLECULES PER CELL FROM THE CALIBRATION CURVE

FIG. 7

FLUORESCENT CALIBRATION MICROBEADS SIMULATING STAINED CELLS

CROSS REFERENCE TO RELATED APPLICATIONS

This is a division of co-pending application Ser. No. 805,654, filed Dec. 11, 1985, which in turn is a continuation-in-part of co-pending application Ser. No. 685,464, filed Dec. 24, 1984.

TECHNICAL FIELD

The invention relates to uniform, polymeric, fluorescent microbeads, the synthesis thereof and their use in aligning and calibrating flow cytometry, fluorescent microscopes, and other instruments.

BACKGROUND ART AND REFERENCE DESCRIPTION

The majority of analytical cytology is conducted using highly sophisticated instruments such as fluorescence microscopes and flow cytometers to examine, count, or otherwise analyze cells stained with fluorescent dyes. Without fluorescent calibration standards, it is not possible to make quantitative determinations about the cells with respect to their fluorescence intensities.

With fluorescence microscopes, it would be useful to have fluorescent calibrated particles which have the same size and fluorescent spectral properties as the stained cells. Such particles could be used to optimize the alignment of the microscope. If such particles had calibrated numbers of fluorescent molecules on them, they could be used as an internal quantitative standard, i.e., mixed with the cells on a slide to compare the brightnesses of cells and particles. Quantitative estimates of the fluorescence intensity of the cells could be made by eye, or accurate measurements could be made with photocells attached to the fluorescent microscope.

Flow cytometry is the process of analyzing and sorting cells in a flowing stream. This is accomplished by intersecting the stream with an incident light, usually a laser, and detecting the resulting scattered light and fluorescence of the individual cells as a function of the particular physical characteristics or attached fluorescent dye, respectively. In addition, electronic volume sensing has also been incorporated in some flow cytometry instruments. With this array of detectors, sub-populations of cells can be analyzed and sorted in arbitrary terms by just detecting their qualitative differences. However, without size and fluorescent standards, no quantitative information on the individual cells can be gained other than the number of them counted and their proportion relative to the rest of the sample.

To determine quantitative differences between sub-populations of cells, and moreover, to give individual populations a quantitative relevance, standards are necessary with known amounts of fluorescence to which these cell samples can be compared. In FIG. 1, a microbead containing a fluorescent dye, fluorescein isothiocynate (FITC), is shown along with a cell labeled with the same dye. If a series of such microbeads containing varying amounts of the fluorescent dye is run on a flow cytometer, the resulting distributions will be obtained, as shown in FIG. 2, indicated by "Bead 1, Bead 2, and Bead 3". Now if a cell population stained with the same dye is also run on the flow cytometer under the same conditions, then the fluorescence intensity of the cells can be quantitatively compared to those of the calibrated microbeads.

Various fluorescent particles have been used in conjunction with flow cytometry including fixed cells, pollen, fluorescent microbeads, and stained nuclei. However, their use has been limited for the most part to instrument alignment and size calibration. Quantitation of fluorescence intensity of cell samples has been hampered by not having a highly uniform, stable particle which has the same excitation and emission spectra as the cells being measured. Those particles which contain the proper dyes, e.g., the fluorescein stained nuclei (marketed as Fluorotrol-GF by Ortho Diagnostic Systems, Inc.) are not stable over long periods of time and those which are considered stable, e.g., the microbeads, have not contained the same dyes which stain the cells. Highly uniform fluorescent microbeads have been available from various sources for a number of years. However, none of these beads have been suitable as quantitative standards for flow cytometry instruments because (1) many of these fluorescent microbeads are smaller than the cells to be analyzed and (2) the fluorescent dyes which have been incorporated into the small microbeads are different from those attached to the cells and (3) beads which are the preferable size (about 4-10 microns in diameter) have been expensive to produce and difficult to obtain because the techniques used in their production give particles of wide variability in size, shape, and other physical properties.

Attempts have been made to cross-calibrate microbeads containing one dye against solutions or cells containing a different dye, e.g., cumerin containing microbeads against fluorescein solutions. However, such a calibration is only good for the one excitation and emission filter system. Use of slightly different filter systems, which may occur with instruments from different manufacturers, can significantly alter the quantitative results. As recognized in parent application Ser. No. 685,464, the key to having a useful fluorescent standard which can be used on any instrument or filter system is for the microbead to have the same excitation and emission spectra as the sample. A more subtle point recognized by the invention is that the environment of the dye molecules can have a large effect on the fluorescence spectra. This is demonstrated in FIG. 3, where the emission intensity of a cell labeled with fluorescein is compared to that of microbeads with fluorescein on the surface and fluorescein within the body of the hydrophobic microbead. The surface fluorescenated microbead has the fluorescein in contact with the aqueous medium, and has the same emission properties as a function of wavelength as does the fluorescein labeled cell suspended in an aqueous medium, whereas, the microbead with the fluorescein within the hydrophobic bead body has a very different response because both the excitation and emission spectra have shifted and broadened as a function of the dye being in a hydrophobic medium and not in contact with water. The related spectra as recognized by the invention are shown in FIG. 4.

Recently, larger microbeads suitable for size calibration of biological cells have been synthesized in outer space (see NASA TM 78132 "Large-size Monodisperse Latexes as a Commercial Space Product", and U.S. Pat. No. 4,247,434). In addition, U.S. Pat. No. 4,336,173 to Ugelstad discloses a method for preparing uniform microbeads of a size suitable for flow cytometry calibration in a conventional, earth-bound laboratory. However, none of these large microbeads were reported to contain a fluorescent dye. Moreover, synthesis as described in U.S. Pat. No. 4,336,173 was found to be hampered by agglomeration and high doublet formation. Even with the suggested polymeric stabilizers, the yields of mono-dispersed microbeads were lower than acceptable. The present invention has for its object, among others, the accomplishment of this task.

In the Ugelstad method, a dispersion of small, uniform, seed particles produced by conventional means is contacted with a first swelling agent which is absorbed into the particles to cause some swelling of the particles. Subsequently, a second swelling agent, usually a polymerizable monomer, is likewise absorbed into the particles. Upon internal polymerization of this monomer, the particle undergoes additional swelling. The desired particle size is reached by absorbing pre-calculated amounts of the first and second substances into the microparticle.

Ugelstad teaches that, when using an oil soluble polymerization initiator which is somewhat soluble in water, the initiator may be added after the monomer has diffused into the particles or it may be dissolved in the monomer before the latter diffuses into the particles (see Ugelstad; at column 6, line 65 to column 7, line 2). Ugelstad further teaches that, when using oil soluble initiators which are less water soluble, it will be necessary to add the initiator together with the first swelling agent (see column 7, lines 2-5). When manufacturing beads, however, adding the initiator with the first swelling agent is disadvantageous because the initiator is unstable and swelled beads containing it must be handled carefully and used quickly. By not including the initiator in the first swelling agent the manufacturer can make a large stable batch of swelled seed beads which can be stored for years, giving the manufacturer the ability to choose the initiator and second swelling agent flexibly while using the same swelled seeds, and enabling the manufacturer to get more reproducible batches of finished polymerized beads by allowing him to draw from a uniform stock solution of swelled beads. At the same time, however, it is desirable to use less water soluble initiators while manufacturing beads, as such initiators are less likely to cause agglutination among the beads and decrease the yield of monodisperse beads. In other words, the prior art teaches that, in order to get good yields of monodisperse beads, an initiator having a very low solubility in water should be used. However, the prior art further teaches that, when such an initiator is used, it should be added with the first swelling agent, and this requirement deprives the manufacturer of the advantages set forth above.

It is therefore an object of this invention to provide a method of manufacturing relatively large polymeric microbeads so that there is a very high yield of monodisperse beads without requiring the manufacturer to add the initiator to the seed beads at the same time the first swelling agent is added. Other objects will appear as the description proceeds.

DISCLOSURE OF INVENTION

The present invention is based on the synthesis and calibration of a set of highly-uniform, polymeric microbead standards. The microbead standards are used to align and calibrate fluorescent microscopes and flow cytometers over the size and fluorescence range of stained cells. The fluorescent microbeads of the invention exhibit excitation and emission spectra equivalent to those of the samples being measured. The calibration of fluorescence intensity of the microbeads is in terms of number of equivalent soluble fluorescent molecules per microbead.

DESCRIPTION OF DRAWINGS

FIG. 1 schematically illustrates a microbead containing a fluorescent dye compared with a cell labelled with the same dye.

FIG. 2 illustrates the fluorescent intensity distribution of several microbeads run on a flow cytometer.

FIG. 4 compares the spectra of fluorescein loaded microbeads in an aqueous medium compared with being in a non-aqueous medium.

FIG. 5 is a block diagram illustrating the steps for synthesizing the microbeads of the invention.

FIG. 6 is a block diagram of the steps involved in calibrating the fluorescent microbeads of the invention.

FIG. 7 is a block diagram illustrating calibration of an instrument utilizing the invention microbeads.

BEST MODE FOR CARRYING OUT THE INVENTION

Figure 3:
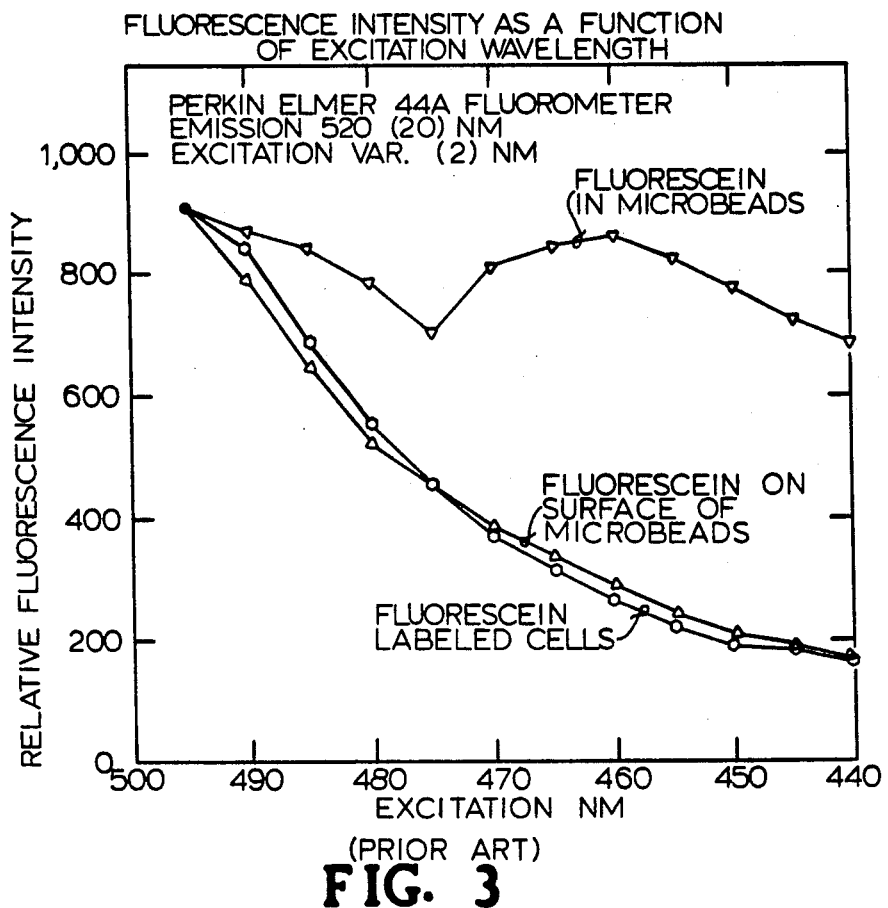
FIG. 3 illustrates a comparison of emission intensity of a fluorescein labelled all with microbeads having fluorescein on the surface and with other microbeads having fluorescein within the body of the microbead.

The synthesis of large-sized microbeads (1-20 microns, preferably 3-9 microns in diameter) is accomplished according to the invention by swelling seed microbeads with two or more substances. The swelling is such that as prescribed by thermodynamics, the enthropy of mixing within the seed microbead allows the seed to swell many times over the amount the seed would swell if mixed with a single substance. While this general approach has been previously described in U.S. Pat. No. 4,336,173, further improvements are critically needed with regard to the stability of the systems and examples described in such patent. Microbeads with less tendency to agglomerate and with less tendency to form doublets are needed. The present invention thus seeks to provide a more satisfactory stability and other improved characteristics in the microbeads.

In the present invention, high concentrations of the oil soluble initiator are dissolved in the oil soluble monomers. This solution is then homogenized with an aqueous surfactant solution prior to using it to swell the microbeads already containing an oil soluble substance. In addition, the invention system is stabilized with alkaline halide salts, preferably potassium chloride, to keep the seeds separated during swelling and polymerization. Once swollen, the suspension is purged with nitrogen and heated to initiate polymerization. It was discovered that the high concentrations of oil soluble initiator (0.5-5%) caused such rapid polymerization within the swollen seeds, that polymerization of monomer in the aqueous phase could not proceed far enough to cause agglutination. It was further observed that any monomer/initiator droplets which were not taken up by the seeds would polymerize individually, since they contained initiator, forming a second smaller population of microbeads and again avoiding agglutination of the other microbeads, especially since the system was stabilized by the addition of salt containing large cations, e.g., potassium. Yields of the large-sized monodispersed microbeads were above 95 percent.

More specifically, the invention method is directed to making microbeads of highly uniform and pre-determined size. The microbeads are prepared from a dispersion of polymeric microparticles, hereinafter referred to as seed particles, which are highly uniform in size but substantially smaller than the size of a cell. The dispersion of seed particles is contacted with a first swelling agent, which should be a substance of one or more materials having a molecular weight of less than 1000 and a water solubility of less than $10^{-3}$ g/l. The preferred first swelling agent is 1-chlorododecane. Other first swelling agents could be selected from the group consisting of cetyl alcohol, 1-chlorononane, 1-bromododecane and 1-dodecanol. Seed beads may be formed of polyvinyl chloride, polyvinyl toluene, styrene, or methylmethacrylate with polyvinyl toluene preferred.

The general guidelines provided by U.S. Pat. No. 4,336,173 are considered helpful in practicing the present invention and are incorporated herein by reference. Important distinctions between the material being incorporated herein and the method of the present invention are later indicated.

The second swelling agent of the invention will always be comprised of one or more polymerizable monomers. If the bead is to be made fluorescent or have some other material connected to its surface, it is desirable to have an ethylenically unsaturated compound having a three-membered epoxy ring as one of the monomers. Representative epoxy monomers include unsaturated alkyl glycidyl esters, unsaturated alkyl glycidyl ethers, unsaturated cycloalkyl glycidyl ethers, unsaturated alkyl-substituted phenyl glycidyl ethers, and the monoepoxide compounds of the diene type monomers.

Suitable glycidyl esters include glycidyl methacrylate, glycidyl acrylate, glycidyl esters of crotonic acid and long chain unsaturated fatty acids and the like; unsaturated alkyl glycidyl ethers include vinyl glycidyl ether, isopropenyl glycidyl ether, oleyl glycidyl ether, allyl and methallyl glycidyl ethers and the like, unsaturated cycloalkyl and phenyl glycidyl ethers include 4-vinyl cyclohexyl glycidyl ether, p-vinylbenzyl glycidyl ether, o-allyl phenylglycidyl ether, and the like; the monoepoxide compounds of the diene type monomers include butadiene monoepoxide, chloroprene monoepoxide, 3,4-epoxy-1-pentene, 4,5-epoxy-1-hexene, 3,4-epoxy-1-vinylcyclohexene and divinylbenzene monoxide and the like. The preferred monomer of the foregoing is methyl methacrylate. Second string preferred monomers comprise the group consisting of sytrene, vinyl tolulene, ethyl methacrylate, ethyl acrylate and methyl acrylate.

The monomer having an epoxy ring can be used alone, but is, in the preferred embodiment, combined with a second copolymerizable monomer to form the second swelling agent. This second monomer should be copolymerizable with the other monomer being used to form the second swelling agent. Suitable monomers for this purpose include the monovinylidene carbocyclic monomers, e.g., styrene, alpha-methylstyrene, ar-(t-butyl)styrene, ar-methylstyrene, ar,ar-dimethylstyrene, ar-chlorostyrene, ar-(t-amyl)styrene, ar-bromostyrene, ar-fluorostyrene, ar-cyanostyrene, ar-methoxystyrene, ar-ethylstyrene, ar-hydroxymethylstyrene, ar-ethoxystyrene, a-chloro-ar-methylstyrene, ar,ar-dichlorostyrene, ar,ar-difluorostyrene, vinyl naphthalene, and other such emulsion polymerizable monomers having no more than 26 carbon atoms; esters of alpha,beta-ethylenically unsaturated carboxylic acids which polymerize to form non-film forming polymers, e.g., methyl methacrylate, chloroethyl methacrylate, n-butyl methacrylate, ethyl methacrylate, isobutyl methacrylate, isopropyl methacrylate, phenyl methacrylate, butyl chloroacrylate, cyclohexyl chloroacrylate, ethyl chloroacrylate, methyl chloroacrylate, isopropyl chloroacrylate and other such esters capable of being polymerized to form hard polymers; alpha,beta-ethylenically unsaturated esters of non-polymerizable carboxylic acids, e.g., vinyl benzoate, vinyl toluate, vinyl ar-ethylbenzoate, allyl ar-ethylbenzoate, vinyl trimethylacetate, vinyl pivalate, vinyl trichloroacetate and other such monomers wherein the unsaturated moity has from 2 to 14 carbon atoms and the acid moity has from 2 to 12 carbon atoms; alpha,beta-ethylenically unsaturated nitriles, e.g., such as nitriles having not more than 12 carbon atoms, other polymerizable vinyl monomers such as vinyl chloride, vinyl bromide and the like. Of the foregoing, the preferred monomer, to be used in combination with glycidyl methacrylate to form the second swelling agent, is methyl methacrylate. The copolymerization parameters $r_1$, $r_2$ should match as closely as possible and stil retain the solubility considerations, i.e., the second swelling should be more soluble in water than first swelling agent but still be less than $10^{-3}$ molarity in water. Second string monomers other than those mentioned can include those containing a carboxyl group that can be activated by carbodiimide, e.g., methacrylic acid, a primary amine group which can be activated by aldehydes, e.g., ally amine, or an isiothiocynate group which is self reactive at alkaline Ph.

In the present invention, high concentrations of an oil soluble initiator, 0.5 to 5% by volume, are dissolved in the second swelling agent. This solution is then homogenized with an aqueous surfactant solution prior to using it to swell the microbeads already containing a first swelling agent. Homogenization aids in rapid incorporation of the monomer/initiator solution into the microbead seeds. It is preferred, but not essential, to add a stablizing agent to the dispersion of swelled seed particles before the addition of the second swelling agent. A preferred stabilizing agent is a salt such as solution of an alkali metal halide in an aqueous solution of the emulsifying agent used for the swelling agent. Among the salts which may be used are the chlorides, bromides and iodides of potassium and cesium, with potassium chloride being preferred. The amount of halide salts which may be used is from baout 0.001M-0.1M. Alkali metals forming hydrated ions smaller than potassium, such as sodium and lithium, are less effective as stabilizing agents.

Once swollen, the suspension is purged with nitrogen and heated to initiate polymerization. It was discovered that the high concentrations of oil soluble initiator (0.5-5%) caused such rapid polymerization within the swollen seeds, that polymerization of monomer in the aqueous phase could not proceed far enough to cause agglutination. It was further observed that any monomer/initiator droplets which were not taken up by the seeds would polymerize individually, since they contained initiator, forming a second smaller population of microbeads and again avoiding agglutination of the other microbeads, especially since the system was stabilized by the addition of salt. Yields of the large-sized monodispersed microbeads were approximately 95 percent.

It is crucial that the initiator chosen be soluble in the second swelling agent, and that the solubility of the initiator in the second swelling agent be greater than its solubility in water. Chemicals suitable for use as swelling agents include benzoyl peroxide and dioctanlyl peroxide, with benzoyl peroxide preferred. Lauryl peroxide was tried in the method of the invention, using methyl methacrylate and glycidyl methacrylate as the second swelling agent, but was found not as efficient. These solubility parameters insure that, prior to polymerization, the second swelling agent will be more likely to escape from the beads than initiator. Moreover, most of the initiator that does escape will be contained in droplets of free monomer rather than dissolved in the aqueous phase, thus resulting in decreased free chain polymerization and agglutination. As mentioned above, any droplets of monomer and initiator polymerize separately to form a smaller, easily separated, population of particles.

Microbead Fluorescenation

Figure 8:
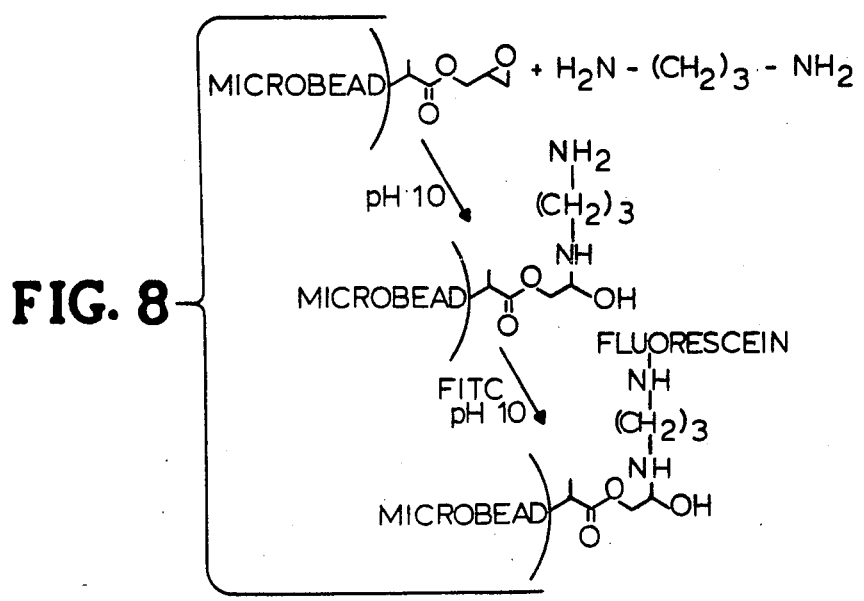
FIG. 8 illustrates microbead surface fluorescenation.

Although fluorescent dyes can be diffused into or copolymerized into the invention microbead, such microbeads may not be useful as fluorescent standards. This is so because incorporation of the dye into a non-aqueous environment can cause spectral shifts in the dye. Such spectral shifts would render the microbead near worthless as quantitative fluorescence standards. To be useful as a quantitative fluorescent standard, the microbeads have to have a functionality on their surface by which the fluorescent dye molecules can be attached. This arrangement maintains the fluorescent dye in the same aqueous environment as that of the cells labeled with the dye, thus retaining equivalent spectra. The preferred functional group on the surface of the large microbead is the epoxy group. It has versatility, in that it can be directly activated under mild conditions, pH 8.5-10, to covalently link with amine-containing dyes, e.g., fluorescein amine or phycoeyrthrine, or it can be linked to a spacer group, e.g., 1,3-diaminopropane or 1,6-diaminohexame which in turn can be linked to a reactive dye, e.g. fluorescein isothiocynate (FITC), under similar mild conditions, pH 8.5-10, to ensure that the dye is surrounded by the aqueous medium. This scheme is illustrated in FIG. 8.

Calibration of the Fluorescent Microbead Standards

Some researchers have attempted to calibrate fluorescent microbeads as well as proteins with radioactive labels in terms of absolute numbers of dye molecules. This approach results in a quagmire of correction factors involving quenching considerations and change in extinction coefficients due to the chemical conjugation of the dye. These problems are reflected by the fact that there are as of yet no NBS accepted primary fluorescent standards for quantitative intensity, let alone for those specific fluorescent dyes of interest in flow cytometry.

Although the idea of quantitation in terms of absolute numbers of molecules of a fluorescent dye is attractive, its practicality at this time is unobtainable. Therefore, an alternative calibration system is provided by means of the present invention which relate a microbead standard back to a stable and reproducible solution of primary standard which has the same excitation and emission spectra as the sample being measured. With sufficiently dilute solutions, considerations of quenching and changes of extinction coefficient may be avoided, as long as the spectra of the primary soluble standard solution, the microbead standards, and the labeled cells in the sample are the same. Thus, fluorescent intensities of a sample may be related to a quantitative concentration of a soluble primary standard via calibrated microbeads which have the same spectra.

The fluorescenated microbeads are calibrated with such a system in terms of Equivalent Soluble Dye Molecules per Microbead. For example, fluorescein microbeads are standardized against a primary laser grade fluorescein. Laser grade fluorescein was chosen because it is the most stable, and of the highest purity, of any of the fluorescein compounds. Also, it has excitation and emission spectra equivalent to that of FITC-labeled cells and the fluorescein microbead standards.

Figure 10:
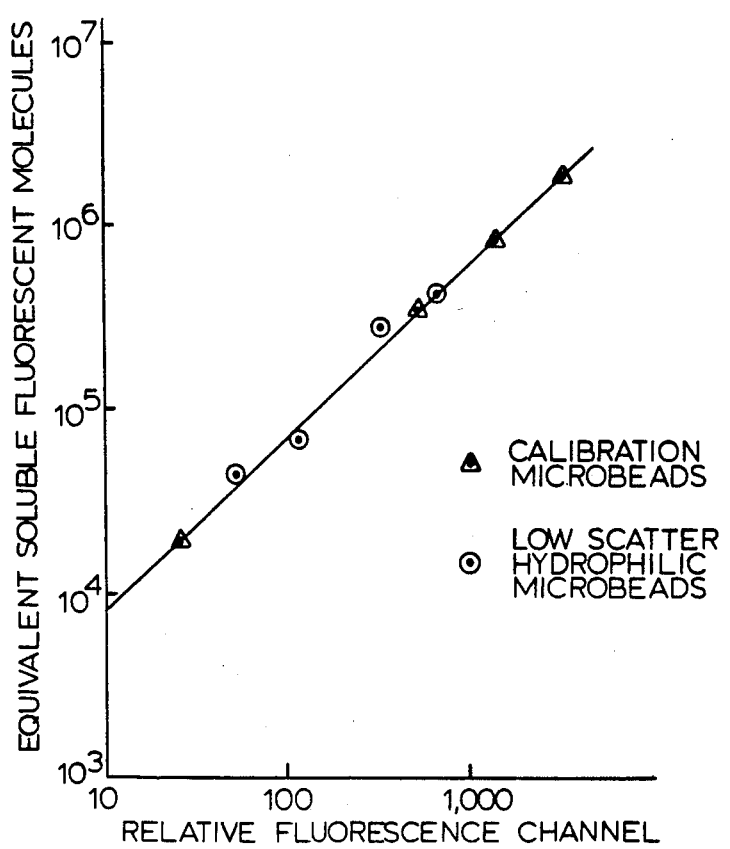
FIG. 10 is a plot on logarithmic scale of Equivalent Soluble Fluorescent Molecules versus Relative Fluorescent Channel.

The fluorescent microbead standards are calibrated by determining the fluorescent intensity of standard solutions of laser grade dyes with a fluorometer and relating those fluorescence intensities to the fluorescence intensity of suspensions of the microbeads. The number of microbeads in the suspension per unit volume is determined with a Coulter Counter TM or a Hemocytometer TM. Then from these data, the number of equivalent soluble dye molecules per microbead is calculated by dividing the equivalent soluble dye molecules per unit volume by the number of microbeads per that unit volume. In the actual practice of calibrating the fluorescent microbead standards, the refractive index of the blank beads (those unfluorescenated) is too high which causes high background scatter (250,000 equivalent soluble dye molecules per microbead). This makes it impossible to directly calibrate them in bulk suspension in a fluorometer. In this case, a different primary microbead whose scatter from the blank microbead is low (1000 equivalent soluble dye molecules per microbead) must be used for calibration against the dye solutions. Such primary microbeads may be synthesized from hydrophillic monomers as 2-hydroxy ethyl methacrylate, methacrylic acid acrylamide, and allyl fluorescein as described in U.S. Pat. Nos. 4,157,323; 4,285,819 and 4,326,008. These primary microbeads are then used to calibrate the flourescence channels of a flow cytometer, and in turn the original flourescent microbead standards are calibrated against the plot developed with the primary microbeads as shown in FIG. 10. These primary microbeads are themselves not as useful as the standard microbeads because they are too small (0.5-1.0 microns), and are not very uniform.

Synthesis of Microbeads

EXAMPLE 1

One milliliter of 1-chlorododecane (CDD) was homogenized with 2.5 ml of 0.25% sodium dodecyl sulfate (SDS) in water and this was added to 5 ml of 10% suspension of 2.02 micron polyvinyl toluene microbeads in 20 ml of SDS solution. Ten milliliters of 30% acetone in water was added to help incorporate the CDD into the microbeads. This was stirred for 12 hours before 1 ml of the suspension was added to 10 ml of distilled water and 20 ml of SDS and evacuated to remove the acetone. Two hundred milligrams (4%) of benzoyl peroxide initiator was dissolved in a 5 ml solution of 95% methyl methacrylate and 5% glycidyl methacrylate before it was homogenized with an equal volume of 0.25% SDS solution. The ten milliliters of the homogenate was then added to the above evacuated suspension of swollen seed microbeads and the suspension was purged with nitrogen and heated to 70° C. for two hours to cause rapid polymerization of the swollen microbeads. The result was a highly uniform microbead with a diameter of 5.3 microns. The yield was 96 percent.

EXAMPLE 2

The procedure was the same as in Example 1, with the exception that 20 ml of homogenized monomers and initiator was added to the seed suspension resulting in microbeads 8.7 microns in diameter.

EXAMPLE 3

The procedure was the same as in Example 1, with the exception that 100 milligrams (2%) of benzoyl peroxide initiator was used. The results were the same as in Example 1.

EXAMPLE 4

The procedure of Example 3 was repeated except 25 mg. of benzoyl peroxide initiator (0.5%) was used. There was increased aggregation of the microbeads indicating 0.5% to be a practical lower limit of initiator concentration. There was a yield of approximately 85%.

Fluorescenation of the Microbeads

EXAMPLE 5

The microbeads in Examples 1 and 2 were washed in 0.25% SDS solution and to them was added an equal volume of 10% 1.3-diaminopropane adjusted to pH 10.0. This was stirred for 12 hours then washed in SDS solution three times and in 0.1M $NaHCO_3$, pH 8.5 two times. FITC was added to portions of these aminated suspensions and then they were washed four times in 0.05 M phosphate buffer pH 7.2. This resulted in green fluorescent microbeads as viewed in an epiluminescent fluorescent microscope using blue exciting light.

EXAMPLE 6

The same procedures was used as in Example 5, except Texas Red was used to replace FITC. The result was red fluorescent microbeads as viewed under the fluorescence microscope using green exciting light.

EXAMPLE 7

The microbeads obtained in Examples 1 and 2, still containing functional epoxy groups, were mixed with a solution of phycoerythrin at a pH of 9.5 for 12 hours. After washing the resulting microbead had an orange fluorescence under the fluorescence microscope.

EXAMPLE 8

The same procedure was carried out as in Example 7, except the microbeads were added to a solution of avidin. Following washing in PBS pH 7.2, the microbeads coated with avidin were exposed to a solution of biotin-phycoerythrin and the microbeads had an orange fluoresence under the fluorescence microscope.

EXAMPLE 9

Figure 9:
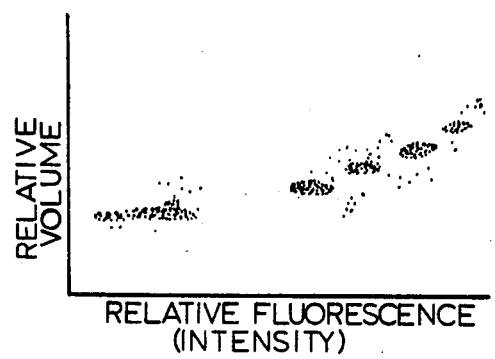
FIG. 9 is a dot plot of a set of five calibration microbeads with varying size and fluorescence intensities.

The microbeads in Example 5 were fluorescenated at predetermined levels of fluorescence intensity with FITC by introducing small amounts of the dyes stepwise into the microbead suspensions and checking the microbeads fluorescence intensity with a flow cytometer. Specifically, 1 mg of FITC was dissolved in 3 ml of methanol and this was added dropwise to a suspension of microbeads from Example 1 in 0.1M $NaHCO_3$ at pH 8.5 while intermittently determining the fluorescence level with a flow cytometer. Only enough FITC methanol solution was added to the microbeads to reach the desired microbead fluorescence intensity. Other suspensions of the same microbeads were brought to different levels of intensity resulting in a set of microbeads of various specific predetermined fluorescence levels, i.e., $2 \times 10^4, 4 \times 10^5, 9 \times 10^5$ and $2 \times 10^6$, which an be used to develop a calibration curve for a flow cytometer as seen in FIGS. 9 and 10.

Calibration

EXAMPLE 10

Step 1

Excitation and emission spectra were taken in PBS pH 7.2 of soluble laser grade fluorescein, hydrophilic (low background scatter) 1 micron microbeads, and the microbeads from Example 6. All the excitation spectra of these samples had a peak at 293 (matched within 3 nanometers) and had equivalent shapes. They also had matching emission spectra with the peak at 518 nanometers.

Step 2

In 1000 mls. of PBS pH 7.2, 9.6 mgs of laser grade fluorescein was dissolved and further diluted 1:100 making a solution of $4.8 \times 10^{-8}$M fluorescein. The fluorescence intensity of this solution was read in a fluorometer and then ratioed against the readings of dilute microbead suspensions (1 million microbeads per ml) to determine the equivalent fluorescein molarity of the microbead suspensions. This molarity was divided by the number of microbeads per ml (1.4 million per ml) as determined with a Hemocytometer. This resulted in $7.8 \times 10^5$ soluble fluorescein molecules per microbead.

Step 3

A set of the small calibrated hydrophilic microbeads were run on a flow cytometer and a calibration plot was made of the microbead fluorescence intensity versus the instrument fluorescent channel number. This calibration curve was then used in turn to quantitate the fluorescence intensity in terms of equivalent soluble fluorescein molecules per microbead of the set of microbeads in Example 9.

Use of the Microbeads

EXAMPLE 11

A set of four fluorescent calibrated microbeads as prepared in Example 9, designated 0(blank), $+1(2 \times 10^4)$, $+2(9 \times 10^5)$, $+3(2 \times 10^6)$, were used with a fluorescence microscope by mixing them with the stained cell samples and comparing them in intensity by eye or with a photocell to the stained cells. The designations 0, +1, +2, +3 are equivalent to the arbitrary assignments given in clinical laboratories and the designations blank, $2 \times 10^4$, $9 \times 10^5$, $2 \times 10^6$, are in terms of equivalent soluble fluorescent molecules per microbead. As long as the microbeads are the same size as the cells being examined, the quantitative estimate of numbers of equivalent soluble fluorescent molecules per cell as determined by comparison to the microbeads will be accurate. Lymphocytes stained with FITC-Leu 1 antibody appear to have the same fluorescence intensity as the +1 microbead and taken to have $2 \times 10^4$ equivalent soluble fluorescein molecules per cell.

EXAMPLE 12

A FACS Analyzer TM (flow cytometer) was calibrated with the microbeads in Example 9. The cells in Example 11 were run on the FACS Analyzer TM without changing any of the instrument settings. This resulted in having the cells fall in a relative intensity channel equal to $2.5 \times 10^4$ equivalent soluble fluorescein molecules per cell.

SUMMARY

The invention in its various aspects provides a method by which a fluorescent microscope or flow cytometer may be calibrated in terms of the number of equivalent soluble fluorescent dye molecules per fluorescence intensity channel of the instrument by the use of highly uniform microbeads with a fluorescent dye associated therewith, such that the microbeads have the same excitation and emission spectra as samples being measured. The invention method is thus based on the microbeads themselves being calibrated in terms of equivalent numbers of soluble fluorescent dye molecules per microbead. Stated differently, the invention method of calibrating the microbeads is based on determining the number of equivalent soluble fluorescent dye molecules necessary to give rise to the same level of fluorescence intensity as the particular microbead. This is accomplished by determining the fluorescence intensity of a suspension of microbeads with a fluorometer as compared to solutions of the free fluorescent dye, and dividing by the number of microbeads in the suspension to yield the number of equivalent soluble fluorescent dye molecules per microbead. When background scatter of these microbeads is too high for direct calibration, a second type of low background scatter hydrophilic microbead is calibrated against the dye solutions and these low background scatter microbeads are then calibrated against the hydrophilic microbeads.

The calibration microbeads useful for the invention have the following properties:

(a) They are highly uniform and in the size range of the sample cells which are being measured, 1-20u in diameter, preferably 3-9u in diameter.

(b) While primarily directed to animal cells ranging from 1-20u in diameter, those skilled in the art will immediately recognize that this invention is applicable to calibration of larger 60-100u cells, such as chloroplasts found in plants.

(c) They have associated with them a fluorescent dye that will give rise to the same excitation and emission spectra as that of the cell sample which is being measured.

(d) They have fluorescence intensities between $10^3$-$10^7$ equivalent soluble molecules of fluorescent dye per microbead.

(e) They are stable with respect to size and fluorescence intensity in their suspending media, which in turn is the same as that in which the cell samples are suspended.

The calibration microbeads are composed of hydrophobic polymeric materials which have chemically functional groups on the surface of the microbeads such that a fluorescent dye may be conjugated via a stable bond, and such that this bonding will maintain the fluorescent dye in contact with the suspension medium. The hydrophobic polymeric materials are preferably a copolymer of 95% methyl methacrylate and 5% glycidyl methacrylate, but the composition could include copolymers in various ratios of styrene, vinyl toluene, and other acrylate and methacrylate esters with glycidyl methacrylate, allyl glycidyl ether, or other epoxy containing monomers.

The preferred method of making the calibration microbead standard is to first swell seed beads with an oil soluble compound, then following with a second swelling with a aqueous homogenate which contains a monomer with a high concentration of oil soluble initiator (0.5–5%) dissolved in it, which will cause polymerization at such a rapid rate in the oil (monomer) phase as to minimize any polymerization in the aqueous phase, thus reducing agglomeration of the microbeads.

The preferred linkage to the microbeads of the fluorescent dye is through a covalent linkage which can be generated by first animating the surface of the microbeads with a diamine, preferably 1,3-diaminopropane or 1,6-diaminohexane, through reacting with the epoxy surface group, then reacting the aminated surface of the microbeads with a reactive fluorescent dye, such as fluorescein isothiocynate or Texas Red. However, a stable linkage can be directly formed to the microbead via the epoxy group reacting directly to a primary amine on the fluorescent dye, such as fluorescein amine or phycoerythrin.

Also to be noted is that sensitivity of the flow cytometer can be determined by using the microbead with the lowest level of fluorescence and a blank microbead, i.e. a microbead without an attached fluorescent molecule, in such a way as to determine the distance between fluorescent peaks of the two microbeads being employed for such purpose.

From the foregoing, it can be seen that the invention not only provides a unique method for calibrating a flow cytometer but also a unique synthesis of the microbead standards related thereto.

What is claimed is:

1. The method of making a calibration microbead standard to minimize aggregation and maximize yield comprising the steps:

(a) homogenizing a highly insoluble ($<10^{-3}$ g/l) compound of molecular weight $<1000$ in a surfactant solution to obtain a first homogenate;

(b) swelling small seed microbeads, 0.1-3u in diameter, with said first homogenate;

(c) homogenizing an aqueous surfactant solution containing a large stabilizing alkaline halide salt with a mixture of oil soluble polymerizable monomers within which is dissolved 0.5-5% by weight an oil soluble initiator to obtain a second homogenate;

(d) swelling the seed microbeads a second time with said second homogenate; and (e) placing said twice swollen microbeads under conditions appropriate to cause said initiator to polymerize the monomers in the swollen microbeads.

2. The method of claim 6 wherein said highly water soluble compound is 1-chlorododecane.

3. The method of claim 6 wherein said stabilizing alkaline halide salt is potassium chloride, said oil soluble monomers methyl methacrylate and glycidyl methacrylate, and said oil soluble initiator is benzoyl peroxide.

* * * * *

UNITED STATES PATENT AND TRADEMARK OFFICE
CERTIFICATE OF CORRECTION

PATENT NO. : 4,714,682
DATED : December 22, 1987
INVENTOR(S) : Abraham Schwartz

It is certified that error appears in the above-identified patent and that said Letters Patent is hereby corrected as shown below:

At Column 6, line 55, change "baout" to --about--.

At Column 12, line 61, change "6" to --1--.

Column 12, line 63, change "6" to --1--.

Signed and Sealed this

Twenty-fourth Day of May, 1988

Attest:

DONALD J. QUIGG

*Attesting Officer*  *Commissioner of Patents and Trademarks*